United States Patent
Kanamaru et al.

(10) Patent No.: US 10,435,732 B2
(45) Date of Patent: Oct. 8, 2019

(54) METHOD FOR PRODUCING RECOMBINANT PROTEINS USING RECOMBINANT BREVIBACILLUS

(71) Applicant: Kaneka Corporation, Osaka (JP)

(72) Inventors: Hiroyuki Kanamaru, Takasago (JP);
Teruaki Takesue, Takasago (JP);
Osamu Odawara, Takasago (JP);
Takeyuki Tsuchidate, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 15/315,116

(22) PCT Filed: Jun. 9, 2015

(86) PCT No.: PCT/JP2015/066561
§ 371 (c)(1),
(2) Date: Nov. 30, 2016

(87) PCT Pub. No.: WO2015/190457
PCT Pub. Date: Dec. 17, 2015

(65) Prior Publication Data
US 2017/0211116 A1    Jul. 27, 2017

(30) Foreign Application Priority Data
Jun. 9, 2014    (JP) .................... 2014-118817

(51) Int. Cl.
*C12P 21/02*    (2006.01)
*C12N 15/00*    (2006.01)
*C12N 15/09*    (2006.01)

(52) U.S. Cl.
CPC .............. *C12P 21/02* (2013.01); *C12N 15/00* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 7,655,452 B1 * | 2/2010 | Hanagata ................. | C12P 21/02 424/93.1 |
| 8,784,819 B2 * | 7/2014 | Yusibov ............. | C12N 15/8258 424/1.49 |
| 2007/0243582 A1 | 10/2007 | Kosugi et al. | |
| 2008/0274525 A1 | 11/2008 | Bramucci et al. | |
| 2010/0152419 A1 * | 6/2010 | Sato ....................... | C07K 14/62 530/303 |
| 2014/0080179 A1 | 3/2014 | Kosugi et al. | |

FOREIGN PATENT DOCUMENTS

| CN | 101691560 A | 4/2010 |
|---|---|---|
| WO | WO-2006/004067 A1 | 1/2006 |
| WO | WO-2008/137403 A1 | 11/2008 |
| WO | WO-2010/001960 A1 | 1/2010 |
| WO | WO-2013/068602 A2 | 5/2013 |

OTHER PUBLICATIONS

Moks et al (*Staphylococcus* protein A consists of five IgG-binding domains. Eur. J. Biochemistry vol. 156, Issue3, 637-643 (1986) (Year: 1986).*
Kato et al (Model for the complex between protein G and an antibody Fc fragment in solution. Structure Jan. 15, 1995, 3:79-85) (Year: 1995).*
Wikstrom et al (Mapping of the Immunoglobulin Light Chain-binding Site of Protein L (J. Mol. Biol. (1995) 250, 128-133 (Year: 1995).*
Use of Bacillus brevis for efficient synthesis and secretion of human epidermal growth factor Proc. Natl. Acad. Sci. USA vol. 86, pp. 3589-3593, May 1989 Biochemistry. (Year: 1989).*
Characterization of Bacillus brevis with Descriptions of *Bacillus migulanus* sp. nov., *Bacillus choshinensis* sp. nov., *Bacillus parabrevis* sp. nov., and *Bacillus galactophilus* sp. nov (International Journal of Systematic Bacteriology, Apr. 1993, p. 221-231) (Year: 1993).*
Anne Farewell Effect of Temperature on In Vivo Protein Synthetic Capacity in *Escherichia coli* Journal of Bacteriology, Sep. 1998, p. 4704-4710). (Year: 1998).*
*Brevibacillus fluminis* sp. nov., isolated from sediment of estuarine wetland. International Journal of Systematic and Evolutionary Microbiology (2010), 60, 1595-1599 (Year: 2010).*
Yan et al., "High-level expression and purification of *Escherichia coli* oligopeptidase B", Protein Expression and Purification, 47 (2006) 645-650.
Kay Terpe, "Overview of bacterial expression systems for heterologous protein production: from molecular and biochemical fundamentals to commercial systems", Appl Microbiol Biotechnol (2006) 72:211-222.
International Preliminary Report on Patentability dated Dec. 15, 2016 in PCT/JP2015/066561. Onishi et al., "Efficient production of anti-fluorescein and anti-lysozyme as single-chain anti-body fragments (scFv) by *Brevibacillus* expression system", Protein Expression and Purification, 91 (2013) 184-191.
San-Miguel et al., "Production of soluble eukaryotic recombinant proteins in *E. coli* is favoured in early log-phase cultures induced at low termperature", SprinterPlus, 2:89, 2013.

* cited by examiner

*Primary Examiner* — Kagnew H Gebreyesus
(74) *Attorney, Agent, or Firm* — Polsinelli PC (57) ABSTRACT

The present invention provides a method for producing a recombinant protein, which can increase the cell growth rate in culture while stably maintaining plasmids in the cells, thereby improving the recombinant protein yield. The present invention provides a method for producing a recombinant protein, including a high-temperature culture step of culturing at 32° C. or higher a *Brevibacillus* bacterium that contains a gene encoding a recombinant protein, and a low-temperature culture step of culturing the *Brevibacillus* bacterium at a temperature lower than 32° C. after the high-temperature culture step.

12 Claims, 1 Drawing Sheet

Specification includes a Sequence Listing.

SEQUENCE LISTING

```
<160> NUMBER OF SEQ ID NOS: 29

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45
```

```
Lys Lys Leu Asn Glu Ser Gln Ala Pro Lys
    50                  55
```

<210> SEQ ID NO 4
<211> LENGTH: 58
<212> TYPE: PRT
<213> ORGANISM: Staphylococcus aureus

<400> SEQUENCE: 4

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 5
<211> LENGTH: 58
<212> TYPE: PRT
<213> ORGANISM: Staphylococcus aureus

<400> SEQUENCE: 5

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 6
<211> LENGTH: 55
<212> TYPE: PRT
<213> ORGANISM: Unknown
<220> FEATURE:
<223> OTHER INFORMATION: Streptococcus

<400> SEQUENCE: 6

```
Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55
```

<210> SEQ ID NO 7
<211> LENGTH: 55
<212> TYPE: PRT
<213> ORGANISM: Unknown
<220> FEATURE:
<223> OTHER INFORMATION: Streptococcus

<400> SEQUENCE: 7

```
Thr Tyr Lys Leu Val Ile Asn Gly Lys Thr Leu Lys Gly Glu Thr Thr
1               5                   10                  15
```

-continued

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Asp Ala Thr
            35                  40                  45

Lys Thr Phe Thr Val Thr Glu
        50                  55

<210> SEQ ID NO 8
<211> LENGTH: 55
<212> TYPE: PRT
<213> ORGANISM: Unknown
<220> FEATURE:
<223> OTHER INFORMATION: Streptococcus

<400> SEQUENCE: 8

Thr Tyr Lys Leu Val Ile Asn Gly Lys Thr Leu Lys Gly Glu Thr Thr
1               5                   10                  15

Thr Lys Ala Val Asp Ala Glu Thr Ala Glu Lys Ala Phe Lys Gln Tyr
            20                  25                  30

Ala Asn Asp Asn Gly Val Asp Gly Val Trp Thr Tyr Asp Asp Ala Thr
            35                  40                  45

Lys Thr Phe Thr Val Thr Glu
        50                  55

<210> SEQ ID NO 9
<211> LENGTH: 76
<212> TYPE: PRT
<213> ORGANISM: Peptostreptococcus magnus

<400> SEQUENCE: 9

Lys Glu Glu Thr Pro Glu Thr Pro Glu Thr Asp Ser Glu Glu Glu Val
1               5                   10                  15

Thr Ile Lys Ala Asn Leu Ile Phe Ala Asn Gly Ser Thr Gln Thr Ala
            20                  25                  30

Glu Phe Lys Gly Thr Phe Glu Lys Ala Thr Ser Glu Ala Tyr Ala Tyr
            35                  40                  45

Ala Asp Thr Leu Lys Lys Asp Asn Gly Glu Tyr Thr Val Asp Val Ala
        50                  55                  60

Asp Lys Gly Tyr Thr Leu Asn Ile Lys Phe Ala Gly
65                  70                  75

<210> SEQ ID NO 10
<211> LENGTH: 72
<212> TYPE: PRT
<213> ORGANISM: Peptostreptococcus magnus

<400> SEQUENCE: 10

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Ala Leu
        35                  40                  45

Lys Lys Asp Asn Gly Glu Tyr Thr Val Asp Val Ala Asp Lys Gly Tyr
        50                  55                  60

Thr Leu Asn Ile Lys Phe Ala Gly
65                  70

<210> SEQ ID NO 11

```
<211> LENGTH: 72
<212> TYPE: PRT
<213> ORGANISM: Peptostreptococcus magnus

<400> SEQUENCE: 11

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Leu Leu
        35                  40                  45

Ala Lys Glu Asn Gly Lys Tyr Thr Val Asp Val Ala Asp Lys Gly Tyr
    50                  55                  60

Thr Leu Asn Ile Lys Phe Ala Gly
65                  70

<210> SEQ ID NO 12
<211> LENGTH: 72
<212> TYPE: PRT
<213> ORGANISM: Peptostreptococcus magnus

<400> SEQUENCE: 12

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Ala Glu Ala Thr Ala Glu Ala Tyr Arg Tyr Ala Asp Leu Leu
        35                  40                  45

Ala Lys Glu Asn Gly Lys Tyr Thr Ala Asp Leu Glu Asp Gly Gly Tyr
    50                  55                  60

Thr Ile Asn Ile Arg Phe Ala Gly
65                  70

<210> SEQ ID NO 13
<211> LENGTH: 73
<212> TYPE: PRT
<213> ORGANISM: Peptostreptococcus magnus

<400> SEQUENCE: 13

Lys Lys Val Asp Glu Lys Pro Glu Glu Lys Glu Gln Val Thr Ile Lys
1               5                   10                  15

Glu Asn Ile Tyr Phe Glu Asp Gly Thr Val Gln Thr Ala Thr Phe Lys
            20                  25                  30

Gly Thr Phe Ala Glu Ala Thr Ala Glu Ala Tyr Arg Tyr Ala Asp Leu
        35                  40                  45

Leu Ser Lys Glu His Gly Lys Tyr Thr Ala Asp Leu Glu Asp Gly Gly
    50                  55                  60

Tyr Thr Ile Asn Ile Arg Phe Ala Gly
65                  70

<210> SEQ ID NO 14
<211> LENGTH: 71
<212> TYPE: PRT
<213> ORGANISM: Peptostreptococcus magnus

<400> SEQUENCE: 14

Lys Glu Thr Pro Glu Pro Glu Glu Glu Val Thr Ile Lys Ala Asn Leu
1               5                   10                  15

Ile Phe Ala Asp Gly Ser Thr Gln Asn Ala Glu Phe Lys Gly Thr Phe
```

```
                20                  25                  30
Ala Lys Ala Val Ser Asp Ala Tyr Ala Tyr Ala Asp Ala Leu Lys Lys
            35                  40                  45

Asp Asn Gly Glu Tyr Thr Val Asp Val Ala Asp Lys Gly Leu Thr Leu
        50                  55                  60

Asn Ile Lys Phe Ala Gly Lys
65                  70

<210> SEQ ID NO 15
<211> LENGTH: 71
<212> TYPE: PRT
<213> ORGANISM: Peptostreptococcus magnus

<400> SEQUENCE: 15

Lys Glu Lys Pro Glu Glu Pro Lys Glu Val Thr Ile Lys Val Asn
1               5                  10                  15

Leu Ile Phe Ala Asp Gly Lys Thr Gln Thr Ala Glu Phe Lys Gly Thr
            20                  25                  30

Phe Glu Glu Ala Thr Ala Lys Ala Tyr Ala Tyr Ala Asp Leu Leu Ala
            35                  40                  45

Lys Glu Asn Gly Glu Tyr Thr Ala Asp Leu Glu Asp Gly Gly Asn Thr
        50                  55                  60

Ile Asn Ile Lys Phe Ala Gly
65                  70

<210> SEQ ID NO 16
<211> LENGTH: 74
<212> TYPE: PRT
<213> ORGANISM: Peptostreptococcus magnus

<400> SEQUENCE: 16

Lys Glu Thr Pro Glu Thr Pro Glu Glu Pro Lys Glu Glu Val Thr Ile
1               5                  10                  15

Lys Val Asn Leu Ile Phe Ala Asp Gly Lys Ile Gln Thr Ala Glu Phe
            20                  25                  30

Lys Gly Thr Phe Glu Glu Ala Thr Ala Lys Ala Tyr Ala Tyr Ala Asn
            35                  40                  45

Leu Leu Ala Lys Glu Asn Gly Glu Tyr Thr Ala Asp Leu Glu Asp Gly
        50                  55                  60

Gly Asn Thr Ile Asn Ile Lys Phe Ala Gly
65                  70

<210> SEQ ID NO 17
<211> LENGTH: 75
<212> TYPE: PRT
<213> ORGANISM: Peptostreptococcus magnus

<400> SEQUENCE: 17

Lys Glu Thr Pro Glu Thr Pro Glu Glu Pro Lys Glu Glu Val Thr Ile
1               5                  10                  15

Lys Val Asn Leu Ile Phe Ala Asp Gly Lys Thr Gln Thr Ala Glu Phe
            20                  25                  30

Lys Gly Thr Phe Glu Glu Ala Thr Ala Glu Ala Tyr Arg Tyr Ala Asp
            35                  40                  45

Leu Leu Ala Lys Val Asn Gly Glu Tyr Thr Ala Asp Leu Glu Asp Gly
        50                  55                  60

Gly Tyr Thr Ile Asn Ile Lys Phe Ala Gly Lys
65                  70                  75
```

<210> SEQ ID NO 18
<211> LENGTH: 290
<212> TYPE: PRT
<213> ORGANISM: Staphylococcus aureus

<400> SEQUENCE: 18

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60

Lys Glu Gln Gln Asn Ala Phe Tyr Glu Ile Leu His Leu Pro Asn Leu
65                  70                  75                  80

Thr Glu Glu Gln Arg Asn Ala Phe Ile Gln Ser Leu Lys Asp Asp Pro
                85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
    130                 135                 140

Ala Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Ala Phe Ile Gln Ser Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Ala Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 19
<211> LENGTH: 23
<212> TYPE: PRT
<213> ORGANISM: Brevibacillus brevis

<400> SEQUENCE: 19

Met Lys Lys Val Val Asn Ser Val Leu Ala Ser Ala Leu Ala Leu Thr
1               5                   10                  15

Val Ala Pro Met Ala Phe Ala
            20

<210> SEQ ID NO 20
<211> LENGTH: 31
<212> TYPE: PRT
<213> ORGANISM: Brevibacillus brevis

<400> SEQUENCE: 20

Met Lys Lys Arg Arg Val Val Asn Asn Ser Val Leu Leu Leu Leu Leu
1               5                   10                  15

Leu Ala Ser Ala Leu Ala Leu Thr Val Ala Pro Met Ala Phe Ala
            20                  25                  30

<210> SEQ ID NO 21
<211> LENGTH: 36
<212> TYPE: PRT
<213> ORGANISM: Staphylococcus aureus

<400> SEQUENCE: 21

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala
        35

<210> SEQ ID NO 22
<211> LENGTH: 881
<212> TYPE: DNA
<213> ORGANISM: Staphylococcus aureus

<400> SEQUENCE: 22
ctgcagataa caaatttaac aaagaacaac aaaacgcttt ctacgaaatc ctgcacttgc      60
caaaccttac tgaagaacaa cgtaatgctt tcatccaatc cctgaaagat gatccatctg    120
tatccaaaga aattttggca gaggctaaaa aacttaacga cgctcaggcg cctaaggctg    180
ataacaaatt caacaaagaa caacaaaacg cttttttatga atccttcac ctgccaaatc    240
ttacagaaga caacgcaac gcattcattc aaagcttgaa ggatgaccct tccgttagca    300
aagagatcct ggctgaagca aaaagttga atgatgcgca agcaccaaaa gctgataata    360
aattcaacaa gaacaacaa aatgcattct acgaaatctt gcaccttcct aacctgactg    420
aagagcagcg taacgctttt atccagagct gaaagacga tccatctgtc tccaaagaaa    480
ttctcgcaga agcgaagaaa ctgaacgatg ctcaagctcc gaaagcagac aacaaattca    540
ataaggaaca gcaaaacgcg ttttatgaaa ttctgcatct tccaaacttg acagaggaac    600
aacgcaatgc tttcatccaa tccctgaaag atgatccgag cgtttctaag gaaatcttgg    660
ctgaagcaaa aaaactgaac gacgctcaag ctccaaaagc ggataacaag tttaacaaag    720
aacaacaaaa tgctttctac gagatcttgc accttccgaa cctgactgaa gaacaacgta    780
acgcatttat tcagtctttg aaggatgacc catccgtaag caaagagatc ctggcagaag    840
ctaaaaaatt gaatgatgca caagctccaa ataatctag a                          881

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23

-continued ggaattctga tttcactttt tgcattctac a        31

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agtgcactcg cacttactgt        20

<210> SEQ ID NO 25
<211> LENGTH: 361
<212> TYPE: DNA
<213> ORGANISM: Artificial Sequence
<220> FEATURE:
<223> OTHER INFORMATION: Synthetic DNA

<400> SEQUENCE: 25
ggtaccaatt ggcgccgcaa cttttgattc gctcaggcgt ttaataggat gtaattgtga        60
gcggataaca attattctgc atggcttttc tgcgaaagga ggtgcaccgc gcttgcagga      120
ttcgggcttt aaaagaaag atagattaac aacaaatatt ccccaagaac aatttgttta      180
tactggagga ggagaacaca aggtcatgaa aaaagaagg gtcgttaaca gtgtattgct      240
tctgctactg ctagctagtg cactcgcact tactgttgct cccatggctt tcgctgcagg      300
atccgtcgac tctagactcg aggaattcgg taccccgggt tcgaaatcga taagcttctg      360
t      361

<210> SEQ ID NO 26
<211> LENGTH: 44
<212> TYPE: DNA
<213> ORGANISM: Artificial Sequence
<220> FEATURE:
<223> OTHER INFORMATION: Primer

<400> SEQUENCE: 26
ttgctcccat ggctttcgct gcgcaacacg atgaagctca acaa        44

<210> SEQ ID NO 27
<211> LENGTH: 60
<212> TYPE: DNA
<213> ORGANISM: Artificial Sequence
<220> FEATURE:
<223> OTHER INFORMATION: Primer

<400> SEQUENCE: 27
cgggatccct attttggtgc ttgagcatcg tttagctttt tagcttctgc taaaattttc        60

<210> SEQ ID NO 28
<211> LENGTH: 1230
<212> TYPE: DNA
<213> ORGANISM: Brevibacillus brevis
<220> FEATURE:
<221> NAME/KEY: -35_signal
<222> LOCATION: (17)..(23)
<220> FEATURE:
<221> NAME/KEY: -10_signal
<222> LOCATION: (41)..(45)
<220> FEATURE:
<221> NAME/KEY: RBS
<222> LOCATION: (94)..(103)
<220> FEATURE:
<221> NAME/KEY: RBS

```
<222> LOCATION: (186)..(196)
<220> FEATURE:
<221> NAME/KEY: CDS
<222> LOCATION: (206)..(1171)
<220> FEATURE:
<221> NAME/KEY: Signal_peptide
<222> LOCATION: (206)..(295)

<400> SEQUENCE: 28
cgtaccaatt ggcgccgcaa cttttgattc gctcaggcgt ttaataggat gtaattgtga      60
gcggataaca attattctgc atggctttcc tgcgaaagga ggtgcaccgc gcttgcagga     120
ttcgggcttt aaaagaaaag atagattaac aacaaatatt ccccaagaac aatttgttta    180
tactagagga ggagaacaca aggtc atg aaa aaa aga agg gtc gtt aac agt      232
                            Met Lys Lys Arg Arg Val Val Asn Ser
                             1               5 gta ttg ctt ctg cta ctg cta gct agt gca ctc gca ctt act gtt gct      280
Val Leu Leu Leu Leu Leu Leu Ala Ser Ala Leu Ala Leu Thr Val Ala
 10              15                  20                  25 ccc atg gct ttc gct gcg caa cac gat gaa gct caa caa aat gct ttt      328
Pro Met Ala Phe Ala Ala Gln His Asp Glu Ala Gln Gln Asn Ala Phe
                 30                  35                  40 tat caa gtg tta aat atg cct aac tta aac gct gat caa cgt aat ggt      376
Tyr Gln Val Leu Asn Met Pro Asn Leu Asn Ala Asp Gln Arg Asn Gly
             45                  50                  55 ttt atc caa agc ctt aaa gat gat cca agc caa agt gct aac gtt tta      424
Phe Ile Gln Ser Leu Lys Asp Asp Pro Ser Gln Ser Ala Asn Val Leu
         60                  65                  70 ggt gaa gct caa aaa ctt aat gac tct caa gct cca aaa gct gat gcg      472
Gly Glu Ala Gln Lys Leu Asn Asp Ser Gln Ala Pro Lys Ala Asp Ala
     75                  80                  85 caa caa aat aag ttc aac aaa gat caa caa agc gcc ttc tat gaa atc      520
Gln Gln Asn Lys Phe Asn Lys Asp Gln Gln Ser Ala Phe Tyr Glu Ile
 90                  95                 100                 105 ttg aac atg cct aac tta aac gaa gag caa cgc aat ggt ttc att caa      568
Leu Asn Met Pro Asn Leu Asn Glu Glu Gln Arg Asn Gly Phe Ile Gln
                110                 115                 120 agt ctt aaa gac gat cca agc caa agc act aac gtt tta ggt gaa gct      616
Ser Leu Lys Asp Asp Pro Ser Gln Ser Thr Asn Val Leu Gly Glu Ala
            125                 130                 135 aaa aaa tta aac gaa tct caa gca ccg aaa gct gac aac aat ttc aac      664
Lys Lys Leu Asn Glu Ser Gln Ala Pro Lys Ala Asp Asn Asn Phe Asn
        140                 145                 150 aaa gaa caa caa aat gct ttc tat gaa atc ttg aac atg cct aac ttg      712
Lys Glu Gln Gln Asn Ala Phe Tyr Glu Ile Leu Asn Met Pro Asn Leu
    155                 160                 165 aac gaa gaa caa cgc aat ggt ttc atc caa agc tta aaa gat gac cca      760
Asn Glu Glu Gln Arg Asn Gly Phe Ile Gln Ser Leu Lys Asp Asp Pro
170                 175                 180                 185 agt caa agt gct aac ctt tta gca gaa gct aaa aag tta aat gaa tct      808
Ser Gln Ser Ala Asn Leu Leu Ala Glu Ala Lys Lys Leu Asn Glu Ser
                190                 195                 200 caa gca ccg aaa gct gat aac aaa ttc aac aaa gaa caa caa aat gct      856
Gln Ala Pro Lys Ala Asp Asn Lys Phe Asn Lys Glu Gln Gln Asn Ala
            205                 210                 215 ttc tat gaa atc tta cat tta cct aac tta aat gaa gaa caa cgc aat      904
Phe Tyr Glu Ile Leu His Leu Pro Asn Leu Asn Glu Glu Gln Arg Asn
        220                 225                 230 ggt ttc atc caa agc tta aaa gat gac cca agc caa agc gct aac ctt      952
Gly Phe Ile Gln Ser Leu Lys Asp Asp Pro Ser Gln Ser Ala Asn Leu
    235                 240                 245
```

```
tta gca gaa gct aaa aag cta aat gat gca caa gca cca aaa gct gac    1000
Leu Ala Glu Ala Lys Lys Leu Asn Asp Ala Gln Ala Pro Lys Ala Asp
250                 255                 260                 265 aac aaa ttc aac aaa gaa caa caa aat gct ttc tat gaa att tta cat    1048
Asn Lys Phe Asn Lys Glu Gln Gln Asn Ala Phe Tyr Glu Ile Leu His
            270                 275                 280 tta cct aac tta act gaa gaa caa cgt aac ggc ttc atc caa agc ctt    1096
Leu Pro Asn Leu Thr Glu Glu Gln Arg Asn Gly Phe Ile Gln Ser Leu
        285                 290                 295 aaa gac gat cct tca gtg agc aaa gaa att tta gca gaa gct aaa aag    1144
Lys Asp Asp Pro Ser Val Ser Lys Glu Ile Leu Ala Glu Ala Lys Lys
    300                 305                 310 cta aac gat gct caa gca cca aaa tag ggatccgtcg actctagact          1191
Leu Asn Asp Ala Gln Ala Pro Lys
        315                 320 cgaggaattc ggtaccccgg gttcgaaatc gataagctt                          1230

<210> SEQ ID NO 29
<211> LENGTH: 321
<212> TYPE: PRT
<213> ORGANISM: Brevibacillus brevis

<400> SEQUENCE: 29

Met Lys Lys Arg Arg Val Val Asn Ser Val Leu Leu Leu Leu Leu Leu
1               5                   10                  15

Ala Ser Ala Leu Ala Leu Thr Val Ala Pro Met Ala Phe Ala Ala Gln
            20                  25                  30

His Asp Glu Ala Gln Gln Asn Ala Phe Tyr Gln Val Leu Asn Met Pro
        35                  40                  45

Asn Leu Asn Ala Asp Gln Arg Asn Gly Phe Ile Gln Ser Leu Lys Asp
50                  55                  60

Asp Pro Ser Gln Ser Ala Asn Val Leu Gly Glu Ala Gln Lys Leu Asn
65                  70                  75                  80

Asp Ser Gln Ala Pro Lys Ala Asp Ala Gln Gln Asn Lys Phe Asn Lys
                85                  90                  95

Asp Gln Gln Ser Ala Phe Tyr Glu Ile Leu Asn Met Pro Asn Leu Asn
            100                 105                 110

Glu Glu Gln Arg Asn Gly Phe Ile Gln Ser Leu Lys Asp Asp Pro Ser
        115                 120                 125

Gln Ser Thr Asn Val Leu Gly Glu Ala Lys Lys Leu Asn Glu Ser Gln
    130                 135                 140

Ala Pro Lys Ala Asp Asn Asn Phe Asn Lys Glu Gln Gln Asn Ala Phe
145                 150                 155                 160

Tyr Glu Ile Leu Asn Met Pro Asn Leu Asn Glu Glu Gln Arg Asn Gly
                165                 170                 175

Phe Ile Gln Ser Leu Lys Asp Asp Pro Ser Gln Ser Ala Asn Leu Leu
            180                 185                 190

Ala Glu Ala Lys Lys Leu Asn Glu Ser Gln Ala Pro Lys Ala Asp Asn
        195                 200                 205

Lys Phe Asn Lys Glu Gln Gln Asn Ala Phe Tyr Glu Ile Leu His Leu
    210                 215                 220

Pro Asn Leu Asn Glu Glu Gln Arg Asn Gly Phe Ile Gln Ser Leu Lys
225                 230                 235                 240

Asp Asp Pro Ser Gln Ser Ala Asn Leu Leu Ala Glu Ala Lys Lys Leu
                245                 250                 255
```

-continued

```
Asn Asp Ala Gln Ala Pro Lys Ala Asp Asn Lys Phe Asn Lys Glu Gln
            260             265             270

Gln Asn Ala Phe Tyr Glu Ile Leu His Leu Pro Asn Leu Thr Glu Glu
        275             280             285

Gln Arg Asn Gly Phe Ile Gln Ser Leu Lys Asp Asp Pro Ser Val Ser
        290             295             300

Lys Glu Ile Leu Ala Glu Ala Lys Lys Leu Asn Asp Ala Gln Ala Pro
305             310             315             320

Lys
```

METHOD FOR PRODUCING RECOMBINANT PROTEINS USING RECOMBINANT BREVIBACILLUS

CROSS REFERENCE TO RELATED APPLICATIONS

This application is a National Phase filing under 35 U.S.C. § 371 of PCT/JP2015/066561 filed on Jun. 9, 2015; and this application claims priority to Application No. 2014-118817 filed in Japan on Jun. 9, 2014 under 35 U.S.C. § 119. The entire contents of each application is hereby incorporated by reference.

TECHNICAL FIELD

The present invention relates to methods for producing a recombinant protein using a recombinant microorganism.

BACKGROUND ART

Processes for production of recombinant proteins using recombinant microorganisms have been used to obtain various heterologous proteins (Non Patent Literature 1). Various culture conditions have been studied to improve recombinant protein productivity. An effective way to improve productivity per unit time is increasing cell growth rate. Generally, the cell growth rate is known to increase as the culture temperature rises as long as the rise is within the range in which microorganisms can grow. At high culture temperatures, however, plasmids introduced into recombinant microorganisms for expression of heterologous proteins are less likely to be stably maintained in the cells and therefore more likely to be lost from the cells. Thus, the recombinant protein yield decreases even though the cells grow rapidly. At low culture temperatures, on the other hand, the plasmids can be stably maintained, but in this case the cell growth rate decreases so that productivity is reduced.

The demand for antibody drugs, among protein drugs produced using recombinant DNA techniques, has been rapidly increasing.

Antibody drugs are generally produced by affinity chromatography based on antibody-binding capacity. The most commonly used chromatography techniques are those that use carriers for antibody purification obtained by immobilizing a protein such as Protein A, Protein G, or Protein L on an appropriate resin. A particularly commonly used ligand having antibody-binding capacity is Protein A.

The affinity carriers using proteins as the ligands are required to have high quality as materials for drug production. Since the ligand proteins themselves are also required to have the same quality level as protein drugs and thus their production cost is high, the affinity carriers have not been available at low cost. The production cost of affinity carriers, which occupies a large portion of the production cost of antibody drugs, has been a major obstacle to reducing the production cost of antibody drugs. Therefore, there is a need for a method for preparing high-quality but inexpensive ligand proteins.

The inventors have already found a method for stably mass-producing a partial sequence of Protein A, which can cause *Brevibacillus* bacterial host cells to efficiently express and secrete large amounts of the partial sequence of Protein A, stably accumulate the protein in the culture fluid, and separate and collect it easily at high purity (Patent Literature 1).

CITATION LIST

Patent Literature

Patent Literature 1: WO 06/004067

Non Patent Literature

Non Patent Literature 1: Kay Terpe. Appl Microbaiol Biotechnol 72: 211-222 (2006)

SUMMARY OF INVENTION

Technical Problem

The present invention provides a method for producing a recombinant protein using a *Brevibacillus* bacterium, which can increase the cell growth rate in culture while stably maintaining plasmids in the cells, thereby improving the recombinant protein yield.

Solution to Problem

As a result of extensive research to solve the above problem, the inventors have surprisingly found that a combination of a high-temperature culture step of performing culture at high temperatures in the first half of the culture process and a low-temperature culture step of performing culture at lower temperatures in the second half of the culture process can increase the growth rate of *Brevibacillus* cells while stably maintaining plasmids in the cells, thereby improving the recombinant protein yield. Based on this finding, the inventors have completed the present invention.

Specifically, the present invention relates to a method for producing a recombinant protein, including: a high-temperature culture step of culturing at 32° C. or higher a *Brevibacillus* bacterium that contains a gene encoding the recombinant protein; and a low-temperature culture step of culturing the *Brevibacillus* bacterium at a temperature lower than 32° C. after the high-temperature culture step.

Preferably, a shift from the high-temperature culture step to the low-temperature culture step is made between the early and mid-exponential growth phases of the *Brevibacillus* bacterium.

Preferably, the recombinant protein is an antibody-binding protein.

Preferably, the antibody-binding protein is selected from the E domain, D domain, A domain, B domain, or C domain of Protein A, the C domain or D domain of Protein G, the B domain of Protein L, proteins containing the foregoing domains connected together, or functional variants of the foregoing.

Preferably, the recombinant protein is a bioactive protein.

Preferably, the bioactive protein is a peptide hormone or a precursor thereof.

Preferably, the recombinant protein is an antibody or antibody-like molecule.

Advantageous Effects of Invention

The present invention provides a process for production of a recombinant protein using a *Brevibacillus* bacterium, which can increase the cell growth rate while stably maintaining plasmids in the cells, thereby improving the recombinant protein yield at reduced cost. Moreover, the method of the present invention can be scaled up to an industrial scale.

DESCRIPTION OF EMBODIMENTS

The present invention relates to a method for producing a recombinant protein, including a high-temperature culture step of culturing at 32° C. or higher a *Brevibacillus* bacterium that contains a gene encoding the recombinant protein, and a low-temperature culture step of culturing the *Brevibacillus* bacterium at a temperature lower than 32° C. after the high-temperature culture step.

Examples of the recombinant protein include antibody-binding proteins, antibodies, antibody-like molecules, enzymes, and other useful bioactive proteins.

Antibody-binding proteins refer to proteins capable of binding to regions (e.g. Fc region) of antibodies other than antigen-recognition sites. Any protein capable of binding to regions of antibodies other than antigen-recognition sites may be used regardless of the structure of the protein. Examples of such proteins include the E domain, D domain, A domain, B domain, or C domain of Protein A, the C domain or D domain of Protein G, the B domain of Protein L, proteins containing the foregoing domains connected together, and functional variants of the foregoing.

Protein A is a type of cell wall protein produced by the Gram-positive bacterium *Staphylococcus aureus*, and has a molecular weight of about 42,000. Protein A has a structure consisting of seven functional domains (from the amino terminus, a signal sequence S, an immunoglobulin-binding domain E, an immunoglobulin-binding domain D, an immunoglobulin-binding domain A, an immunoglobulin-binding domain B, an immunoglobulin-binding domain C, and a *Staphylococcus aureus* cell wall-binding domain X) (Proc. Natl. Acad. Sci. USA, 1983, 80: 697-701; Gene, 1987, 58: 283-295; J. Bio. Chem., 1984, 259: 1695-1702).

The relative affinity of each immunoglobulin-binding domain of Protein A is known to depend on many factors such as pH, *Staphylococcus aureus* strain (Infec. Immun., 1987, 55: 843-847), and immunoglobulin class (IgG, IgM, IgA, IgD, IgE) and subclass (IgG1, IgG2, IgG3, IgG4, IgA1, IgA2). These domains strongly bind particularly to the Fc regions of immunoglobulins of the following classes: human IgG1, human IgG2, human IgG4, mouse IgG2a, mouse IgG2b, and mouse IgG3.

Examples of the E domain, D domain, A domain, B domain, and C domain of Protein A include proteins having the amino acid sequences of SEQ ID NO:1, SEQ ID NO:2, SEQ ID NO:3, SEQ ID NO:4, and SEQ ID NO:5, respectively.

Protein G is a type of cell wall protein produced by group C and group G *Streptococcus* bacteria, and has a molecular weight of about 59,000. Protein G has a structure consisting of five functional domains (from the amino terminus, a signal sequence SS, an albumin-binding domain with repeated sequences A and B, an immunoglobulin-binding domain with repeated sequences C and D, a cell wall-penetrating domain W, and a cell membrane-penetrating domain M).

The immunoglobulin-binding domain of Protein G shows binding to the Fc regions of a wider range of mammalian IgGs than the immunoglobulin-binding domains of Protein A (J. Immunol., 1984, 133: 969-974; J. Biol. Chem., 1991, 266: 399-405).

Examples of the C domain or D domain of Protein G include proteins having the amino acid sequences of SEQ ID NO:6, SEQ ID NO:7, and SEQ ID NO:8.

Protein L is a type of protein produced by *Peptostreptococcus magnus*, and has a molecular weight of about 79,000. Protein L has a structure consisting of six functional domains (from the amino terminus, a single sequence SS, an amino terminus domain A, five repeated immunoglobulin-binding domains B, two repeated domains C whose function is unknown, a cell wall-penetrating domain W, and a cell membrane-penetrating domain M).

The immunoglobulin-binding domain of Protein L shows binding to the κ light chains of immunoglobulins (J. Biol. Chem., 1989, 264: 19740-19746; J. Biol. Chem., 1992, 267: 12820-12825).

Examples of the B domain of Protein L include proteins having the amino acid sequence of SEQ ID NO:9, SEQ ID NO:10, SEQ ID NO:11, SEQ ID NO:12, SEQ ID NO:13, SEQ ID NO:14, SEQ ID NO:15, SEQ ID NO:16, and SEQ ID NO:17.

Functional variants of the antibody-binding proteins refer to antibody-binding protein variants that have antibody-binding activity. The functional variants preferably have at least 60%, more preferably at least 65%, still more preferably at least 70%, even more preferably at least 75%, further preferably at least 80%, yet further preferably at least 85%, particularly preferably at least 90%, most preferably at least 95% sequence identity to the C domain of Protein A of SEQ ID NO:5.

Proteins containing the antibody-binding proteins connected together refer to proteins obtained by connecting the antibody-binding proteins in series. They may be obtained by connecting different antibody-binding proteins or the same antibody-binding proteins. The number of antibody-binding proteins connected may be, for example, 2, 3, 4, 5, 6, 7, 8, 9, or 10. Examples of the proteins containing the antibody-binding proteins connected together include a protein having the amino acid sequence of SEQ ID NO:18 which contains five functional variants of the C domain of Protein A.

Examples of the antibodies and antibody-like molecules include full-length antibodies such as IgG, IgM, IgA, IgD, and IgE, and antibody fragments with the antigen-binding sites thereof.

Examples of the enzymes include amylases, proteases, cellulases, lipases, cholesterol oxidases, alcohol dehydrogenases, amino acid dehydrogenases, D-amino acid oxidases, L-amino acid oxidases, transaminases, esterases, acylases, amidases, hydantoinases, hydantoin racemases, decarbamylases, nitrilases, nitrile hydratases, N-acylamino acid racemases, D-succinylases, L-succinylases, carbamylamino acid racemases, amino acid amide racemases, aminopeptidases, and oxygenases.

Other useful bioactive proteins refer to proteins used as pharmaceutically active components, such as insulin, interferons, interleukins, erythropoietins, growth hormones, peptide hormones, cytokines, growth factors, hematopoietic factors, and precursors thereof, and receptor proteins thereof.

The gene encoding the recombinant protein may be any gene having a base sequence encoding the recombinant protein. DNA containing the gene can be acquired by conventionally known methods such as polymerase chain reaction (hereinafter, abbreviated as PCR) methods. The DNA can also be synthesized by known chemical synthesis methods (Nucleic acids Res. 1984. 12: 4359) or available from DNA libraries. The codons in the DNA may be replaced by degenerate codons.

An expression vector may be used to cause a *Brevibacillus* bacterium to express the recombinant protein. The expression vector contains a gene encoding the recombinant protein. The promoter used to express the gene may be a promoter that can function in *Brevibacillus* bacteria.

Any promoter that can function in *Brevibacillus* bacteria may be used. The promoter is preferably a promoter that is derived from a bacterium such as *Escherichia coli*, *Bacillus subtilis*, or species of the genera *Brevibacillus, Staphylococcus, Streptococcus, Streptomyces*, and *Corynebacterium*, and is operable in *Brevibacillus* bacteria. It is more preferably a promoter of a gene encoding a middle wall protein (MWP) or an outer wall protein (OWP), each of which is a cell wall protein of *Brevibacillus* bacteria, or a *Brevibacillus choshinensis* HPD31 cell wall protein HWP (Ebisu. S. et al., J. Bacteriol. 1990. 172: 1312-1320). Specific examples include the P5 promoter region of a *Brevibacillus brevis* cell wall protein MWP and the P2 promoter region of a *Brevibacillus brevis* cell wall protein MWP.

The expression vector preferably further contains, downstream of the promoter, a Shine-Dalgarno sequence and a signal sequence which can function in *Brevibacillus* bacteria. The Shine-Dalgarno sequence is preferably one that is derived from a bacterium such as *Escherichia coli*, *Bacillus subtilis*, or species of the genera *Brevibacillus, Staphylococcus, Streptococcus, Streptomyces*, and *Corynebacterium*, and is operable in *Brevibacillus* bacteria. It is more preferably a Shine-Dalgarno sequence located upstream of a gene encoding a middle wall protein (MWP) or an outer wall protein (OWP), each of which is a cell wall protein of *Brevibacillus* bacteria, or a *Brevibacillus choshinensis* HPD31 cell wall protein HWP. The expression vector may contain a marker sequence if desired.

The expression vector may contain, downstream of the Shine-Dalgarno sequence, a DNA sequence encoding a secretory signal peptide. The DNA sequence encoding a secretory signal peptide needs not to be the same as the original DNA sequence as long as it is translated by *Brevibacillus brevis* to encode the same amino acids as those of the original DNA sequence. The secretory signal peptide is preferably, for example, one that is derived from a bacterium such as *Escherichia coli*, *Bacillus subtilis*, or species of the genera *Brevibacillus, Staphylococcus, Streptococcus, Streptomyces*, and *Corynebacterium*, and is operable in *Brevibacillus* bacteria. It is more preferably a secretory signal peptide of a middle wall protein (MWP) or an outer wall protein (OWP), each of which is a cell wall protein of *Brevibacillus* bacteria, or a *Brevibacillus choshinensis* HPD31 cell wall protein HWP. The secretory signal peptide used may also be one obtained by modifying the amino acid sequence of a conventional secretory signal peptide.

Specific examples of the secretory signal peptide include a secretory signal peptide of a middle wall protein (MWP), and secretory signal peptides in which basic or hydrophobic amino acid residues, for example, are added to or deleted from the sequence (SEQ ID NO: 19)
Met-Lys-Lys-Val-Val-Asn-Ser-Val-Leu-Ala-Ser-Ala-
Leu-Ala-Leu-Thr-Val-Ala-Pro-Met-Ala-Phe-Ala
as underlined in (SEQ ID NO: 20)
Met-Lys-Lys-<u>Arg-Arg</u>-Val-Val-Asn-Asn-Ser-Val-<u>Leu-
Leu-Leu-Leu-Leu</u>-Leu-Ala-Ser-Ala-Leu-Ala-Leu-Thr-
Val-Ala-Pro-Met-Ala-Phe-Ala.

Secretory signal peptides conventionally used in *Brevibacillus* secretory proteins can also be used.

The secretory signal peptide may also be the original signal peptide of Protein A, i.e. Met-Lys-Lys-Lys-Asn-Ile-Tyr-Ser-Ile-Arg-Lys-Leu-Gly-Val-Gly-Ile-Ala-Ser-Val-Thr-Leu-Gly-Thr-Leu-Leu-Ile-Ser-Gly-Gly-Val-Thr-Pro-Ala-Ala-Asn-Ala (SEQ ID NO:21).

The promoter, Shine-Dalgarno sequence, and secretory signal peptide-encoding DNA can be obtained from *Brevibacillus* bacteria, for example. They may preferably be obtained by known PCR-based specific amplification methods using as template chromosomal DNA of *Brevibacillus brevis* 47 (JCM6285), *Brevibacillus brevis* 47K (FERM BP-2308), *Brevibacillus brevis* 47-5 (FERM BP-1664), *Brevibacillus choshinensis* HPD31 (FERM BP-1087), *Brevibacillus choshinensis* HPD31-S (FERM BP-6623), or *Brevibacillus choshinensis* HPD31-OK (FERM BP-4573).

In the expression vector, the promoter, the Shine-Dalgarno sequence, the signal peptide sequence, and the recombinant protein-encoding gene are preferably linked to be operable in *Brevibacillus* bacteria.

The expression vector is preferably a plasmid vector. Specific examples of plasmid vectors useful in the expression of genes of *Brevibacillus* bacteria include pUB110 known as a *Bacillus subtilis* vector, pHY500 (JP H02-31682 A), pNY700 (JP H04-278091 A), pHY4831 (J. Bacteriol. 1987. 1239-1245), pNU200 (Shigezo Udaka, Nippon Nogeikagaku Kaishi, 1987. 61: 669-676), pNU100 (Appl. Microbiol. Biotechnol., 1989, 30: 75-80), pNU211 (J. Biochem., 1992, 112: 488-491), pNU211R2L5 (JP H07-170984 A), pNH301 (Shiga. Y. et al., Appl. Environ. Microbiol. 1992. 58: 525-531), pNH326, pNH400 (Ishihara. T et al., 1995. J. Bacteriol, 177: 745-749), pHT210 (JP H06-133782 A), pHT110R2L5 (Appl. Microbiol. Biotechnol., 1994, 42: 358-363), and pNCMO2 which is a shuttle vector between *Escherichia coli* and *Brevibacillus* bacteria (JP 2002-238569 A). Moreover, a method may also be used which includes directly incorporating into the chromosome an expression vector containing a promoter capable of functioning in *Brevibacillus* bacteria, a Shine-Dalgarno sequence, and a DNA sequence encoding a target protein, or a gene fragment containing these sequences, followed by expression (JP H09-135693 A).

The recombinant protein may be produced by methods that involve or do not involve secretion in *Brevibacillus* bacteria, but a method in which the recombinant protein is secreted into the culture fluid is preferred for easy separation and purification.

In order to secrete the recombinant protein into the culture fluid, a DNA encoding a signal peptide that functions in *Brevibacillus* bacteria is preferably added or linked upstream of the gene encoding the recombinant protein.

The host cell used to obtain a transformant may be any *Brevibacillus* bacterium. Non-limiting examples of the *Brevibacillus* bacterium include *Brevibacillus agri*, *Brevibacillus borstelensis*, *Brevibacillus brevis*, *Brevibacillus centrosporus*, *Brevibacillus choshinensis*, *Brevibacillus formosus*, *Brevibacillus invocatus*, *Brevibacillus laterosporus*, *Brevibacillus limnophilus*, *Brevibacillus parabrevis*, *Brevibacillus reuszeri*, and *Brevibacillus thermoruber*.

The *Brevibacillus* bacterium is preferably selected from the group consisting of *Brevibacillus brevis* 47 (JCM6285),

*Brevibacillus brevis* 47K (FERM BP-2308), *Brevibacillus brevis* 47-5 (FERM BP-1664), *Brevibacillus brevis* 47-5Q (JCM8970), *Brevibacillus choshinensis* HPD31 (FERM BP-1087), *Brevibacillus choshinensis* HPD31-S (FERM BP-6623), *Brevibacillus choshinensis* HPD31-OK (FERM BP-4573) and *Brevibacillus choshinensis* SP3 (available from Takara Bio Inc.). The above *Brevibacillus brevis* 47, *Brevibacillus brevis* 47-5Q, *Brevibacillus choshinensis* HPD31, *Brevibacillus choshinensis* SP3, *Brevibacillus choshinensis* HPD31-OK, and *Brevibacillus choshinensis* HPD31-S are particularly suitable.

Mutants of the *Brevibacillus* bacterium, such as protease-deficient mutants or high-expression mutants, can also be used. Examples of the mutants include *Brevibacillus choshinensis* HPD31-OK which is a protease-deficient mutant derived from *Brevibacillus choshinensis* HPD31 (JP H06-296485 A) and *Brevibacillus brevis* 47K which is a human salivary amylase high-producing mutant (Konishi, H. et al., Appl Microbiol. Biotechnol. 1990. 34: 297-302). Also, mutants of any strain selected from the group of the *Brevibacillus* bacteria mentioned above may be used.

Of the microorganisms mentioned above, *Brevibacillus brevis* 47K (FERM BP-2308), *Brevibacillus brevis* 47-5 (FERM BP-1664), *Brevibacillus choshinensis* HPD31 (FERM BP-1087), *Brevibacillus choshinensis* HPD31-S (FERM BP-6623), and *Brevibacillus choshinensis* HPD31-OK (FERM BP-4573) have been deposited under their accession numbers with International Patent Organism Depositary, National Institute of Advanced Industrial Science and Technology (IPOD; Tsukuba Central 6, 1-1-1 Higashi, Tsukuba, Ibaraki, 305-8566, Japan). *Brevibacillus brevis* 47 (JCM6285) and *Brevibacillus brevis* 47-5Q (JCM8970) are available from Microbe Division (Japan Collection of Microorganisms (JCM)), RIKEN BioResource Center (3-1-1, Koyadai, Tsukuba, Ibaraki 305-0074, Japan). The *Brevibacillus* bacteria mentioned above can be used as received without any modification such as mutation, or alternatively, *Brevibacillus* bacteria that show higher recombinant protein yield or quality may further be acquired from the aforementioned *Brevibacillus* bacteria before use in the production of the recombinant protein.

When microorganisms including *Brevibacillus* bacteria are caused to highly express heterologous proteins, the formed proteins are often incorrectly folded and inactive. Particularly when proteins containing many disulfide bonds are to be highly expressed, they are also often insolubilized intracellularly and extracellularly. It is also known that in the expression of a target protein, the insolubilization of the target protein and the deterioration in secretion efficiency thereof can be reduced by the action of, for example, chaperone proteins, or disulfide bond isomerases and/or proline isomerases. Methods have been widely attempted which involve the action of proteins having disulfide oxidation-reduction activity such as protein disulfide isomerase (PDI) and/or DsbA (JP S63-294796 A, JP H05-336986 A).

Furthermore, methods are also known for producing proteins having correct disulfide bonds by introducing a gene encoding a protein having disulfide oxidation-reduction activity into a host organism to coexpress a target protein and the protein having disulfide oxidation-reduction activity (e.g. JP 2000-83670 A, JP 2001-514490 T).

Also in the expression of the recombinant protein according to the present invention, several types of folding-promoting enzymes such as chaperone proteins, disulfide bond oxidoreductases, and/or disulfide isomerases may be coexpressed in order to reduce the burden on host cells caused by excessive protein synthesis and smoothly effect protein secretion. Specifically, *Escherichia coli* DsbA that is involved in disulfide bonding of proteins and thought to be a protein disulfide isomerase analog (Bardwell, J. C. A. et al., Cell. 1991. 67: 582-589; Kamitani. S et al., EMBO. J. 1992. 11: 57-62) and/or chaperone proteins such as DnaK, DnaJ, or GrpE (JP H09-180558 A) may be coexpressed in the protein expression in *Brevibacillus* bacteria. Alternatively, folding-promoting enzymes such as the enzyme PDI involved in correct disulfide bonding of polypeptides (JP 2001-567367), disulfide oxidoreductases (JP 2003-169675 A) (Kontinen, V, P. et al., Molecular Microbiology. 1993. 8: 727-737), and/or disulfide isomerases may be coexpressed with the protein to further improve secretion efficiency.

The *Brevibacillus* bacterial host cell can be transformed with the gene encoding a recombinant protein by the following known methods: the method of Takahashi et al. (Takahashi. W et al., J. Bacteriol. 1983. 156: 1130-1134), the method of Takagi et al. (Takagi. H. et al., 1989. Agric. Biol. Chem., 53: 3099-3100), or the method of Okamoto et al. (Okamoto. A. et al., 1997. Biosci. Biotechnol. Biochem. 61: 202-203).

The medium used for culturing the *Brevibacillus* bacterium may be any medium that allows for high-efficiency and high-yield production of the recombinant protein. Specifically, carbon and nitrogen sources such as glucose, sucrose, glycerol, polypeptone, meat extracts, yeast extracts, and casamino acid can be employed. In addition, the medium may be supplemented with inorganic salts such as potassium salts, sodium salts, phosphates, magnesium salts, manganese salts, zinc salts, and iron salts. If necessary, compounds may be added which have an antifoaming effect (e.g. soybean oil, lard oil, surfactants) or which are expected to change the substance permeability of cell membranes to improve recombinant protein secretion yield per cell. It is preferred to use surfactants because they may enhance the effect of the present invention. Any surfactant may be used as long as it does not adversely affect the growth of the recombinant *Brevibacillus* bacterium and/or the production of the recombinant protein. Preferred are polyoxyalkylene glycol surfactants. When auxotrophic host cells are used, nutritional substances necessary for their growth may be added. Antibiotics such as penicillin, erythromycin, chloramphenicol, and neomycin may also be added. Protease inhibitors known in the art may be added in order to reduce the degradation and low-molecularization of the target protein due to host-derived intracellular or extracellular proteases. Examples of the protease inhibitors include phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetraacetic acid (EDTA).

The concentration of the carbon source contained in the medium at the start of culture is preferably 1% or higher or 10% or lower, more preferably initially 1-10%. It is still more preferred to additionally add the carbon source as appropriate during the culture to maintain a carbon source concentration of 10% or lower, 5% or lower, 3% or lower, or particularly 1% or lower. The carbon source may be additionally added in portions or continuously.

The culture may be carried out aerobically under aerated and agitated conditions or anaerobically without aeration. Aerobic culture is preferred. The culture can be performed at a pH of 4 to 9, preferably 5 to 8. The culture may also be carried out either batchwise or continuously.

The production method of the present invention includes a high-temperature culture step of culturing the *Brevibacillus* bacterium at 32° C. or higher, and a low-temperature culture step of culturing the *Brevibacillus* bacterium at a temperature lower than 32° C. after the high-temperature culture step. In the high-temperature culture step and low-temperature culture step, the *Brevibacillus* bacterium is cultured in a liquid medium or solid medium.

In the high-temperature culture step of culturing the *Brevibacillus* bacterium at 32° C. or higher, the *Brevibacillus* bacterium is cultured at a temperature of 32° C. or higher from the start of culture. The culture temperature in the high-temperature culture step is preferably 32° C. to 60° C., more preferably 32° C. to 50° C., still more preferably 32° C. to 40° C. A culture temperature of higher than 60° C. tends to lower cell growth, while a culture temperature of lower than 32° C. tends to decrease cell growth rate.

In the low-temperature culture step of culturing the *Brevibacillus* bacterium at a temperature lower than 32° C. after the high-temperature culture step, the *Brevibacillus* bacterium is cultured at a temperature lower than 32° C. The culture temperature in the low-temperature culture step is preferably at least 10° C. but lower than 32° C., more preferably at least 15° C. but lower than 32° C., still more preferably at least 20° C. but lower than 32° C., even more preferably at least 25° C. but lower than 32° C. A culture temperature of 32° C. or higher tends to lead to unstable plasmid maintenance in the cells, while a culture temperature of lower than 10° C. tends to lower cell growth.

Preferably, a shift from the high-temperature culture step to the low-temperature culture step is made between the early and mid-exponential growth phases of the *Brevibacillus* bacterium. The shift from the high-temperature culture step to the low-temperature culture step made between the early and mid-exponential phases has the effect of increasing the cell growth rate in culture while stably maintaining plasmids in the cells, thereby improving the recombinant protein yield.

Exponential growth phases generally refer to phases during which all the cells contained in the culture system divide and multiply at certain intervals so that the total number of cells in the entire culture system doubles each time, and therefore the log of cell number plotted against the time axis appears straight. Since the achieved cell density of the *Brevibacillus* bacterium depends on the type of medium used, the exponential growth phases cannot be defined based on the absolute value of turbidity of the medium. The exponential growth phases are therefore defined using the relative turbidity (%) of the used medium as an index, where the turbidity of the medium when it shows the maximum cell density is taken as 100%. With this index, the early exponential growth phase of the *Brevibacillus* bacterium is a phase in which the relative turbidity of the medium is 1 to 35%, while the mid-exponential growth phase of the *Brevibacillus* bacterium is a phase in which the relative turbidity of the medium is higher than 35% but not higher than 70%.

With the above index, the shift from the high-temperature culture step to the low-temperature culture step is preferably made when the relative turbidity is 1 to 70%, more preferably 5 to 60%, still more preferably 10 to 50%, further more preferably 15 to 40%.

The shift from the high-temperature culture step to the low-temperature culture step is made by changing the preset temperature of the culture apparatus to reduce the temperature of the liquid medium used in the high-temperature culture step. The shift from the high-temperature culture step to the low-temperature culture step usually does not require medium replacement, but the medium may be replaced.

The turbidity of the medium refers to the absorbance of the medium measured at a wavelength of 600 nm with a spectrophotometer.

Since a large amount of the recombinant protein produced is accumulated extracellularly, i.e., in the culture supernatant, the recombinant protein can be collected and purified from the culture supernatant. The recombinant protein present within and on the surface of the cells can also be collected by disrupting the cells by known methods, such as using ultrasonication, French press, alkali treatment, or SDS treatment. The protein collected from the culture supernatant or cells can be purified by, for example, salting-out using ammonium sulfate, sodium sulfate or other salts, concentration using ethanol, acetone or other solvents, gel filtration, ion exchange, hydroxyapatite, or chromatography based on the affinity of the recombinant protein.

EXAMPLES

Hereinafter, the present invention is described in detail with reference to examples which, however, are not intended to limit the scope of the present invention. In the examples, the preparation and manipulation of recombinant DNA and other operations were carried out in accordance with the following experiment books, unless otherwise stated: (1) T. Maniatis, E. F. Fritsch, J. Sambrook, "Molecular Cloning/A Laboratory Manual" Vol. 2 (1989), Cold Spring Harbor Laboratory (US); and (2) ed. M. Muramatsu, "Laboratory Manual for Genetic Engineering" Vol. 3 (1996), Maruzen Publishing Co., Ltd. The reagents, restriction enzymes and other materials used in the examples were commercially available ones, unless otherwise stated.

(Production Example 1) Preparation of Transformant Expressing Five Connected Functional Variants of C Domain of Protein a The amino acid sequence of a protein obtained by substituting Gly at position 29 of the C domain of Protein A by Ala and then connecting five C-domain variants (SEQ ID NO:18, hereinafter referred to as C-G29A) was reverse-translated to design a DNA sequence encoding this protein. The codons were distributed so that the codon frequency of the protein was close to the codon frequency of HWP, which is a cell surface protein expressed in large amounts in *Brevibacillus choshinensis* HPD31 (J. Bacteriol., 172, pp. 1312-1320, 1990), and that the sequence identity of the base sequences encoding the five respective domains was low. Further, a PstI restriction enzyme recognition site was created on the 5'-side of the sequence encoding the five connected domains, while an XbaI restriction enzyme recognition site was created on the 3'-side thereof. The sequence of the prepared DNA fragment is shown in SEQ ID NO:22. The prepared DNA fragment was digested with PstI and XbaI (both available from Takara Bio, Inc.) and fractionated and purified by agarose gel electrophoresis. Meanwhile, pNCMO2 (available from Takara Bio, Inc.), which is a plasmid vector for *Brevibacillus* bacteria, was digested with PstI and XbaI and then purified and collected. These fragments were mixed and then ligated with Ligation High (available from Toyobo Co., Ltd.) to construct a plasmid vector pNCMO2-C-G29A. *Brevibacillus choshinensis* SP3 (available from Takara Bio, Inc.) was transformed with the plasmid vector to produce a *Brevibacillus choshinensis* SP3(pNCMO2-C-G29A).

(Reference Example 1) Comparison in Recombinant Protein C-G29A Yield and Plasmid Retention Between *Brevibacillus choshinensis* SP3(pNCMO2-C-G29A) Bacteria Cultured at Different Temperatures The *Brevibacillus choshinensis* SP3(pNCMO2-C-G29A) bacteria obtained in Production Example 1 were cultured in a medium A (1.5% peptone, 0.4% yeast extract, 2% glucose, 0.38% phosphate, 0.02% $MgSO_4 \cdot 7H_2O$, 0.002% $MnSO_4 \cdot 4H_2O$, 0.002% $FeSO_4 \cdot 7H_2O$, 0.0002% $ZnSO_4 \cdot 7H_2O$, pH 7.2, continuously supplemented with 3.8% glucose from 6 to 48 hours after the start of culture) to which 750 ppm of Disfoam CC-118 was added, at the following culture temperatures: 28, 30, 32, 34, and 36° C., under aerobic conditions at a controlled pH of 7.0 to 7.2.

The culture fluids were sampled 46 hours after the start of culture, and the plasmid retention of the *Brevibacillus choshinensis* bacteria in the culture fluids was measured by the following method. First, each culture fluid sample was appropriately diluted with 0.9% physiological saline, and 100 µl of the dilution was applied to a standard agar medium (available from Nissui Pharmaceutical Co., Ltd.) plate, followed by static culture at 30° C. for 20 hours. The colonies produced on the plate were replicated on a standard agar medium plate containing 60 ppm neomycin, followed by static culture at 30° C. for 24 hours. Then, the plasmid retention of the bacteria was determined from the growth of colonies.

The culture fluids were also sampled 67 hours after the start of culture, and the cells were removed from each culture fluid by centrifugation (15,000 rpm, 25° C., 5 minutes). Then, the concentration of the recombinant protein C-G29A in the culture supernatants was measured by high performance liquid chromatography. Table 1 shows the concentrations of the recombinant protein C-G29A and plasmid retentions at the different culture temperatures.

TABLE 1

| Culture temperature (° C.) | C-G29A concentration (g/L) | Plasmid retention (%) |
|---|---|---|
| 28 | 4.8 | 100 |
| 30 | 5.1 | 100 |
| 32 | 4.5 | 75 |
| 34 | 4.7 | 44 |
| 36 | 4.3 | 25 |

As shown in Table 1, stable plasmid maintenance (100% plasmid retention) was observed at culture temperatures of 28° C. and 30° C., whereas decreases in plasmid retention and also in concentration of the recombinant protein C-G29A in the culture supernatant were observed at culture temperatures of 32° C. or higher.

(Example 1) Temperature Shift Culture Process 1 of *Brevibacillus choshinensis* SP3(pNCMO2-C-G29A)

The *Brevibacillus choshinensis* SP3(pNCMO2-C-G29A) bacteria obtained in Production Example 1 were cultured in a medium A (continuously supplemented with 4.8% glucose from 6 to 30 hours after the start of culture) to which 750 ppm of Disfoam CC-118 was added, under aerobic conditions at a controlled pH of 7.0 to 7.2. The culture was carried out under the following conditions: the culture temperature was 36° C. for 13.5 hours from the start of culture, and then after the relative turbidity of the medium reached 33% the temperature was shifted and maintained at 30° C. until the end of culture.

The culture fluid was sampled 41 hours after the start of culture, and the concentration of the recombinant protein C-G29A in the culture supernatant was measured as in Reference Example 1. Also, the culture fluid was sampled 41 hours after the start of culture, and the turbidity of the sample at 600 nm was analyzed with a spectrophotometer. The culture fluid was also sampled 46 hours after the start of culture, and the plasmid retention was measured as in Reference Example 1. Table 2 shows the results.

(Comparative Example 1) Culture Process 1 of *Brevibacillus choshinensis* SP3(pNCMO2-C-G29A)

The same procedure as in Example 1 was followed, but using a constant culture temperature of 30° C. from the start of culture to the end of culture. Table 2 shows the results.

TABLE 2

| | Culture temperature (° C.) | C-G29A concentration (g/L) | Turbidity | Plasmid retention (%) |
|---|---|---|---|---|
| Example 1 | 36→30 | 5.6 | 64.0 | 100 |
| Comparative Example 1 | 30 | 4.5 | 59.0 | 100 |

As shown in Table 2, Example 1 in which the culture temperature was shifted showed a great increase in concentration of the recombinant protein C-G29A in the culture supernatant compared to Comparative Example 1 using a constant culture temperature of 30° C. Example 1 also showed an increase in turbidity, which is indicative of the amount of cells, compared to Comparative Example 1. Moreover, the plasmid retention after 46 hours from the start of culture measured for the culture at constant 36° C. was extremely low (25%) as shown in Table 1, whereas the culture process with a temperature shift from 36° C. to 30° C. exhibited stable plasmid maintenance (100% plasmid retention) even after 46 hours from the start of culture.

(Example 2) Temperature Shift Culture Process 2 of *Brevibacillus choshinensis* SP3(pNCMO2-C-G29A)

The *Brevibacillus choshinensis* SP3(pNCMO2-C-G29A) bacteria obtained in Production Example 1 were cultured in a medium A to which 750 ppm of Disfoam CC-118 was added, under aerobic conditions at a controlled pH of 7.0 to 7.2. The culture was carried out under the following conditions: the culture temperature was 34° C. for 13.5 hours from the start of culture, and then after the relative turbidity of the medium reached 22% the temperature was shifted and maintained at 30° C. until the end of culture.

The culture fluid was sampled 37 hours after the start of culture, and the concentration of the recombinant protein C-G29A in the culture supernatant was measured as in Reference Example 1. Also, the culture fluid was sampled 37 hours after the start of culture, and the turbidity of the sample at 600 nm was analyzed with a spectrophotometer. The culture fluid was also sampled 41 hours after the start of culture, and the plasmid retention was measured as in Reference Example 1. Table 3 shows the results.

(Comparative Example 2) Culture Process 2 of Brevibacillus choshinensis SP3(pNCMO2-C-G29A)

The same procedure as in Example 2 was followed, but using a constant culture temperature of 30° C. from the start of culture to the end of culture. Table 3 shows the results.

TABLE 3

|  | Culture temperature (° C.) | C-G29A concentration (g/L) | Turbidity | Plasmid retention (%) |
|---|---|---|---|---|
| Example 2 | 34→30 | 4.6 | 57 | 100 |
| Comparative Example 2 | 30 | 4.0 | 50 | 100 |

As shown in Table 3, Example 2 in which the culture temperature was shifted showed a significant increase in concentration of the recombinant protein C-G29A in the culture supernatant compared to Comparative Example 2 using a constant culture temperature of 30° C. Example 2 also showed an increase in turbidity, which is indicative of the amount of cells, compared to Comparative Example 2. Moreover, the plasmid retention after 46 hours from the start of culture measured for the culture at constant 34° C. was extremely low (44%) as shown in Table 1, whereas the culture process with a temperature shift from 34° C. to 30° C. exhibited stable plasmid maintenance (100% plasmid retention) even after 41 hours from the start of culture.

(Production Example 2) Construction of Brevibacillus Expression Vector pNK3260

A Brevibacillus expression vector pNK3260 was constructed by replacing the MWP p5 promoter contained in pNH326 (J. Bacteriol., 1995, 177: 745-749) with an MWP P2 promoter as described below. First, PCR was performed using two oligonucleotide primers Primer-1 and Primer-2 having the base sequences of SEQ ID NOs:23 and 24, respectively, with pNH326 as a template to amplify the pNH326 except for the MWP P5 promoter. The amplified fragment was terminally digested with restriction enzymes EcoRI and HindIII (both from Takara Bio, Inc.). Then, a double-stranded DNA fragment containing an MWP P2 promoter having the base sequence of SEQ ID NO:25 was prepared by conventional techniques. The fragment was terminally digested with restriction enzymes MunI and HindIII (both from Takara Bio, Inc.). These two DNA fragments were ligated with T4DNA ligase (from Takara Bio, Inc.) to construct pNK3260.

(Production Example 3) Cloning of Protein A-Encoding DNA Sequence Derived from Staphylococcus aureus Cowan I (JCM2179)

Staphylococcus aureus Cowan I (JCM2179) was shake-cultured overnight at 37° C. in a T2 liquid medium (1% polypeptone, 0.2% yeast extract, 1% glucose, 0.5% fish extract, pH 7.0). The cells were collected from the resulting culture fluid by centrifugation, and then washed twice with 10 mM Tris-HCl buffer (pH 8.0). The cells were suspended in the same buffer, lysed with 1% SDS, and heated at 60° C. for 30 minutes, and then the total genomic DNA was extracted by conventional techniques such as phenol extraction and ethanol precipitation. The Staphylococcus aureus Cowan I (JCM2179) is available from Microbe Division (Japan Collection of Microorganisms (JCM)), RIKEN BioResource Center (3-1-1, Koyadai, Tsukuba, Ibaraki 305-0074, Japan).

Next, two oligonucleotide primers Primer-3 and Primer-4 having the base sequences of SEQ ID NOs:26 and 27, respectively, were prepared based on the DNA sequence information of the Protein A gene (Shuttleworth, H. L et al., Gene, 1987, 58: 283-295). PCR was performed using the two oligonucleotide primers Primer-3 and Primer-4 with the genomic DNA of Staphylococcus aureus Cowan I (JCM2179) as a template to amplify a DNA fragment (about 0.9 kbp) encoding Protein A except for the signal sequence (S domain) and the cell wall-binding domain (X-domain) (hereinafter, such a protein portion is referred to as SPA'). The DNA fragment was digested with restriction enzymes NcoI and BamHI and then separated and collected using an agarose gel.

The Brevibacillus expression vector pNK3260 constructed in Production Example 2 was also digested with restriction enzymes NcoI and BamHI and then purified and collected as described above, followed by dephosphorylation by alkaline phosphatase treatment.

Figure 1:
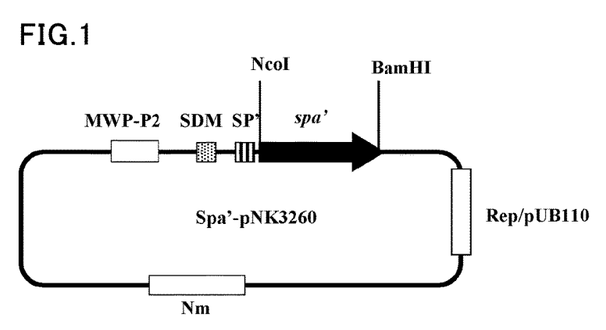
FIG. 1 is a schematic view of expression plasmid Spa'-pNK3260.
Figure 2:
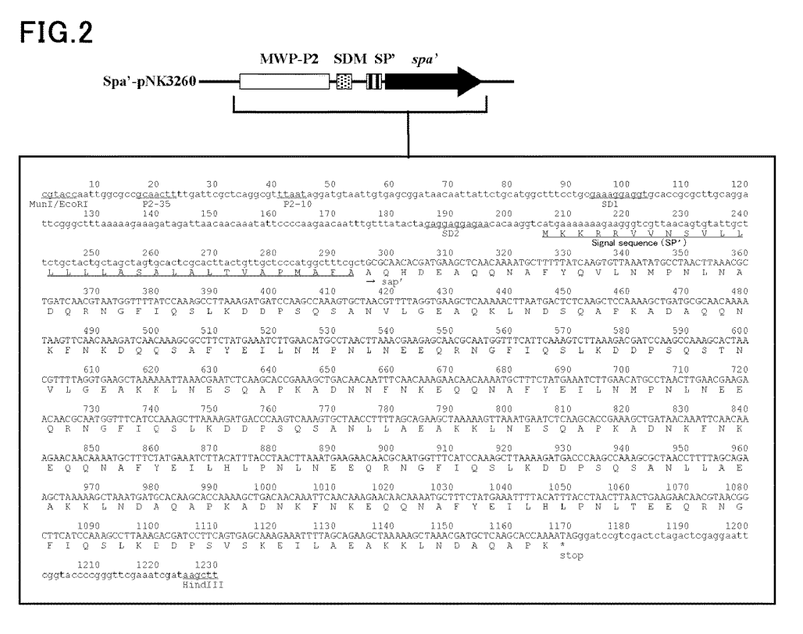
FIG. 2 shows the base sequences of a promoter, Shine-Dalgarno (SD) sequence, and signal peptide- and Protein A (SPA')-encoding DNA in Spa'-pNK3260.

The restriction enzyme treated DNA fragment encoding SPA' and expression vector pNK3260 were ligated with T4DNA ligase to construct an SPA' expression plasmid Spa'-pNK3260 which is shown in FIG. 1. FIG. 2 shows a promoter, SD sequence, and signal peptide- and Protein A (SPA')-encoding DNA in Spa'-pNK3260. The base sequence of SEQ ID NO:28 shows the promoter, SD sequence, and signal peptide- and Protein A (SPA')-encoding DNA in Spa'-pNK3260. SEQ ID NO:29 shows the amino acid sequence encoded by the signal peptide- and Protein A (SPA')-encoding DNA.

In FIG. 1 and FIG. 2, "MWP-P2" represents the P2 promoter region of a Brevibacillus brevis cell wall protein MWP; "SDM" represents the SD sequence of a Brevibacillus brevis cell wall protein MWP; "SP'" represents an altered signal peptide sequence obtained by partially altering the signal peptide sequence of a Brevibacillus brevis cell wall protein MWP; "spa'" represents the DNA sequence encoding SPA'; "Nm" represents the coding region of a neomycin-resistant gene; and "Rep/pUB110" represents the replication origin of the vector pNK3260. Also in FIG. 2, "P2-35" and "P2-10" represent the −35 region and −10 region, respectively, of the P2 promoter of a Brevibacillus brevis cell wall protein MWP.

A transformant Brevibacillus choshinensis HPD31-OK (Spa'-pNK3260) was produced by electroporation of Brevibacillus choshinensis HPD31-OK (FERM BP-4573) with Spa'-pNK3260.

(Example 3) Temperature Shift Culture Process of Brevibacillus choshinensis HPD31-OK(Spa'-pNK3260)

The Brevibacillus choshinensis HPD31-OK(Spa'-pNK3260) obtained in Production Example 3 was cultured in a medium A (continuously supplemented with 5.0% glucose from 6 to 48 hours after the start of culture) to which 750 ppm of Disfoam CC-118 was added, under aerobic conditions at a controlled pH of 7.0 to 7.2. The culture was carried out under the following conditions: the culture temperature was 34° C. for 13.5 hours from the start of culture, and then after the relative turbidity of the medium reached 21% the temperature was shifted and maintained at 30° C. until the end of culture. The culture fluid was sampled 48 hours after the start of culture, and the concentration of the recombinant protein SPA' in the culture supernatant was measured as in Reference Example 1. Also, the culture fluid was sampled 48 hours after the start of culture, and the turbidity of the sample at 600 nm was analyzed with a spectrophotometer. Table 4 shows the results.

(Comparative Example 3) Culture Process of *Brevibacillus choshinensis* HPD31-OK(Spa'-pNK3260)

The same procedure as in Example 3 was followed, but using a constant culture temperature of 30° C. from the start of culture to the end of culture. Table 4 shows the results.

TABLE 4

|  | Culture temperature (° C.) | SPA' concentration (g/L) | Turbidity |
|---|---|---|---|
| Example 3 | 34→30 | 4.8 | 60 |
| Comparative Example 3 | 30 | 3.0 | 40 |

As shown in Table 4, Example 3 in which the culture temperature was shifted showed a great increase in concentration of the recombinant protein SPA' in the culture supernatant compared to Comparative Example 3 using a constant culture temperature of 30° C. Example 3 also showed a great increase in turbidity, which is indicative of the amount of cells, compared to Comparative Example 3.

The invention claimed is:

1. A method for producing a recombinant protein, comprising:
    a high-temperature culture step of culturing in a liquid medium at 34° C. or higher and 40° C. or lower a *Brevibacillus choshinensis* bacterium that contains a gene encoding the recombinant protein;
    a temperature shifting step of reducing the temperature of the liquid medium prepared in the high-temperature culture step without replacing the liquid medium, and
    a low-temperature culture step of culturing the *Brevibacillus choshinensis* bacterium in the liquid medium at a temperature at 25° C. or higher and lower than 32° C., which is lower than the culturing temperature in the high-temperature culture step by at least 2° C.-8° C.

2. The method for producing a recombinant protein according to claim 1,
    wherein a shift from the high-temperature culture step to the low-temperature culture step is made between the early and mid-exponential growth phases of the *Brevibacillus* bacterium.

3. The method for producing a recombinant protein according to claim 1,
    wherein the recombinant protein is an antibody-binding protein.

4. The method for producing a recombinant protein according to claim 3,
    wherein the antibody-binding protein is selected from the E domain, D domain, A domain, B domain, or C domain of Protein A, the C domain or D domain of Protein Cy the B domain of Protein L, proteins comprising the foregoing domains connected together, or functional variants of the foregoing.

5. The method for producing a recombinant protein according to claim, 1 wherein the recombinant protein is a bioactive protein.

6. The method for producing a recombinant protein according to claim 5,
    wherein the bioactive protein is a peptide hormone or a precursor thereof.

7. The method for producing a recombinant protein according to claim 1,
    wherein the recombinant protein is an antibody or antibody-like molecule.

8. The method for producing a recombinant protein according to claim 2, wherein the recombinant protein is an antibody-binding protein.

9. The method for producing a recombinant protein according to claim 8,
    wherein the antibody-binding protein is selected from the E domain, D domain, A domain, B domain, or C domain of Protein A, the C domain or D domain of Protein Cy the B domain of Protein L, proteins comprising the foregoing domains connected together, or functional variants of the foregoing.

10. The method for producing a recombinant protein according to claim 2, wherein the recombinant protein is a bioactive protein.

11. The method for producing a recombinant protein according to claim 10,
    wherein the bioactive protein is a peptide hormone or a precursor thereof.

12. The method for producing a recombinant protein according to claim 2, wherein the recombinant protein is an antibody or antibody-like molecule.

* * * * *